United States Patent
Kislykh et al.

(10) Patent No.: US 6,632,657 B1
(45) Date of Patent: Oct. 14, 2003

(54) APPARATUS FOR CULTIVATING TISSUE CELLS AND MICROORGANISMS IN SUSPENSION

(75) Inventors: Vasily Ivanovich Kislykh, Novosibirsk (RU); Jury Akhmetovich Ramazanov, Novosibirsk (RU); Andrei Petrovich Repkov, Novosibirskaya obl (RU)

(73) Assignee: Biozex Technologies Corp (CA)

( * ) Notice: Subject to any disclaimer, the term of this patent is extended or adjusted under 35 U.S.C. 154(b) by 0 days.

(21) Appl. No.: 09/787,525

(22) PCT Filed: Sep. 22, 1998

(86) PCT No.: PCT/RU98/00296

§ 371 (c)(1),
(2), (4) Date: Mar. 19, 2001

(87) PCT Pub. No.: WO00/17314

PCT Pub. Date: Mar. 30, 2000

(30) Foreign Application Priority Data

Sep. 22, 1998 (RU) ............................................. 98117375

(51) Int. Cl.⁷ ................................................. C12M 1/04
(52) U.S. Cl. ............................... 435/289.1; 435/295.1; 435/302.1; 435/818
(58) Field of Search ................................. 435/383, 243, 435/289.1, 295.1–295.3, 296.1, 300.1, 301.1, 302.1, 818; 366/101–104; 261/119.1, 123

(56) References Cited

U.S. PATENT DOCUMENTS 4,259,449 A   3/1981  Katinger et al.
4,655,918 A * 4/1987  Eertink ........................ 210/199

FOREIGN PATENT DOCUMENTS

| RU | 1650690 | 5/1991 |
| RU | 1779690 | 12/1992 |
| RU | 2099413 | 12/1997 |
| WO | 92/05245 | 4/1992 |
| WO | 93/21301 | 10/1993 |

* cited by examiner

Primary Examiner—William H. Beisner
(74) Attorney, Agent, or Firm—Ostrolenk, Faber, Gerb & Soffen, LLP

(57) ABSTRACT

An apparatus for cultivating tissue cells or microorganisms in suspension, in a manner which ensures formation of an axially symmetric vortex motion of liquid with an axial countercurrent flow in the cell suspension without stagnant zones at various locations. The apparatus has guide elements that stabilize the position of an annular partition with respect to the surface of the suspension, including first blades and second blades. The first blades are attached to the upper surface of the partition with the help of the first struts. The second blades are attached to the lower surface of the partition with the help of the second struts. Each of the first blades and the second blades is provided with a clamping device of "screw-nut" or collet type for varying the angle of attack with respect to the incoming flow of gas and liquid and for securing to the respective strut on the upper surface of the annular partition and at the lower surface of it.

6 Claims, 2 Drawing Sheets

APPARATUS FOR CULTIVATING TISSUE CELLS AND MICROORGANISMS IN SUSPENSION

TECHNICAL FIELD

The present invention relates to biotechnology and more particularly to an apparatus for cultivating tissue cells or microorganisms in suspension.

BACKGROUND ART

An apparatus for cultivating tissue cells and microorganisms in suspension is known in the art (SU, A1, No. 1331888, 1987); which comprises a closed reservoir to the bottom of which branch pipes are connected for feeding an aerating gas. One group of the branch pipes is arranged tangentially, and the other parallel to the cylindrical wall of the reservoir. In the process of cultivating, the aerating gas at once involves the suspension in a vortex motion with simultaneous circulation in the form of ascending and descending streams along the axis of the apparatus.

However, such an apparatus cannot be used for cultivating cells of animal and human tissues: these cells can be easily traumatized, since in the process of cultivating in suspension a large number of gas bubbles is formed, and destruction of these bubbles will cause death of many cells. Aeration by gas blowing leads to the formation of foam which also results in loss of a part of the cells. Foam suppression will require introducing costly non-toxic chemical defoaming agents into the nutrient medium, the technological process of cultivation will be complicated, and the use of defoaming agents will deteriorate the properties of the culture medium.

An apparatus for cultivating tissue cells and microorganisms in suspension is known in the art (U.S. Pat. No. 4,259,449, 1981), which comprises a cylindrical reservoir with a cover and branch pipes for feeding an aerating gas and removing gaseous medium, and a device for stirring the cell suspension, said device being made as a grid disposed in the bottom part of the reservoir. Air is supplied through the grid to the reservoir for creating hydrostatic pressure which prevents precipitation of cells from the suspension.

However, the productivity of such an apparatus in the process of cultivating cells is low owing to worsening of the mass transfer characteristics which, in turn, are impaired, insofar as the intensity of feeding the aerating gas is reduced in order to obviate traumatizing the cells. Even in this case traumatizing the cells cannot be ruled out completely, and intensive foam formation takes place.

Also known in the art is an apparatus for cultivating tissue cells and microorganisms in suspension (WO 92/05245, A1, Feb. 4, 1992), comprising a cylindrical reservoir with a cover and branch pipes for gas feeding and removal, a device for aerating and stirring the suspension. The device for the aeration and stirring comprises a horizontal blade wheel secured on a vertical power shaft and arranged in the top part of the reservoir directly under the cover, and an annular plate placed thereunder, provided with a central opening for the removal of gas, attached over the periphery thereof to the wall of the reservoir, forming an annular space around the blade wheel for gas feeding and removal. Slot openings are provided in the annular partition for the passage of gas, said slots being distributed uniformly along the circumference at an angle to the horizontal plane. The branch pipe for feeding the gas is installed in the cover coaxially with the blade wheel, and the branch pipe for the removal of gas is coupled to said annular space and disposed on the edge of the cover.

The disadvantage of such an apparatus is that formation of vortex motion of liquid (potential vortex with axial reverse flow) therein can be achieved at high gas flow velocities (greater than 15–18 m/s) above the surface of this liquid, i.e., said vortex formation involves considerable power inputs. At the same time, there occurs entrainment of liquid drops from the surface of the suspension with subsequent ejection of these drops onto the wall of the reservoir. Cells in the suspension drops become traumatized by the impact against the wall of the apparatus, i.e., mass death of the cells takes place. With a decrease in the gas flow velocity (6–8 m/s), an unstable flow of the liquid above the surface of the cell suspension is observed, i.e., the axial-symmetric vortex motion of the liquid is periodically changed for auto-oscillations of the liquid, in which mode there originates a wave travelling along the wall of the reservoir. The surface of the liquid becomes curved and represents an asymmetric paraboloid of rotation. All the liquid in the apparatus oscillates as a single whole, the entire apparatus starts rocking, and this produces an unfavorable effect on the cell cultivation process. Besides, the design of the apparatus allows cultivating cells with the reservoir being filled to a height equal to or less than one diameter of this reservoir. If the reservoir is filled with the cell suspension to a height greater than one diameter thereof, a stagnant zone will be formed at the bottom of the reservoir. During cultivation cells will inevitably settle in this zone and perish because of deficiency in oxygen.

An apparatus for cultivating tissue cells or microorganisms in suspension is known, which comprises a cylindrical reservoir with a cover and branch pipes, accordingly, for feeding an aerating gas and removing gaseous medium, and a device for aerating and stirring the suspension, comprising a horizontal blade wheel secured on a vertical hollow shalt and arranged in the top part of the reservoir directly under the cover (WO 93/21301, A1, Oct. 28, 1993—the first embodiment of the apparatus). The device for aerating and stirring the medium is provided with an annular partition installed in the cylindrical reservoir coaxially with the blade wheel, a clearance being formed between the cylindrical wall of the reservoir and the annular partition; the device is also provided with a mechanism for stabilizing the position of the annular partition with respect to the surface of the cell suspension. In accordance with this embodiment of the invention, the mechanism for stabilizing the position of the annular partition with respect to the surface of the cell suspension is made in the form of racks attached to the cover of the reservoir and to the annular partition with help of latches with a possibility of varying the position of the annular partition in relation to the height of the reservoir. The annular partition should be immersed to a depth $H \geq 0.02(D_1 - D_2)$, where $D_1$ is the diameter of the annular partition;

$D_2$ is the diameter of the axial opening in the annular partition.

A disadvantage of this embodiment of the apparatus is as follows. In many cases the process of cultivating cells and tissues is accompanied by changes in the level of the initial filling of the bioreactor (for example, owing to periodic sampling or the cultivation in the initial period being carried out with small volumes of the nutrient medium, whereas the final stage of cultivating is carried out with maximum filling of the reservoir of the reactor). As a result, the depth (H) of immersing the annular partition changes, i.e., the condition $H \geq \geq 0.02(D_1 - D_2)$ is disturbed. A decrease of the value (H) results in "locking" of the liquid drain through the axial opening in the annular partition, and this leads to deterioration of the process of stirring and aerating the cells being cultivated. Should the annular partition hang stationary above the surface of the cell suspension, the mass-transfer parameters will worsen still further. If the depth of immersing (H) of the annular partition is appreciably greater than $H=0.02(D_1-D_2)$, a travelling wave will be formed above the surface of the suspension, which gradually results in rocking the whole mass of the cell suspension, bringing it to the state of unstable stirring with lowered mass-transfer parameters. Therefore, under the conditions of periodic variations in the level of filling the reservoir of the apparatus in the process of cultivating, this device will be either almost inoperable, or introducing an additional mechanism will be required for automatic setting of the annular partition to the optimum depth on variations in the level of filling of the apparatus reservoir. This will make the apparatus much more complicated. Furthermore, the use of a stationary annular partition will involve additional power inputs and time expenditures for the bioreactor to reach the operating mode.

The known prior art most relevant to the proposed technical solution (prototype) is an apparatus for cultivating tissue cells or microorganisms in suspension, which comprises a cylindrical reservoir with a cover and branch pipes, accordingly, for feeding an aerating gas and removing gaseous medium, and a device for aerating and stirring the suspension, comprising a horizontal blade wheel secured on a vertical hollow shaft and arranged in the top part of the reservoir directly under the cover (WO 93/21301, A1, Oct. 28, 1993—the second embodiment of the apparatus). The device for aerating and stirring the medium is provided with an annular partition installed in the cylindrical reservoir coaxially with the blade wheel, a clearance being formed between the cylindrical wall of the reservoir and the annular partition; the device is also provided with a mechanism for stabilizing the position of the annular partition with respect to the surface of the cell suspension. The mechanism for stabilizing the position of the annular partition with respect to the surface of the cell suspension consists of floats with lead blades secured to the upper surface of the annular partition. The annular partition should be immersed to the depth $H \geq 0.02(D_1-D_2)$, where $D_1$ is the diameter of the annular partition;

$D_2$ is the diameter of the axial opening in the annular partition.

The disadvantage of this embodiment of the apparatus (the embodiment with the floating annular partition) is in that for reaching a high density of plant and animal cells in suspension or in cultivating highly aerobic cell cultures, the velocity of the air vortex above the surface of the liquid phase should be greater than 7–8 m/s in order to provide optimum conditions for aerating said biological objects. But with such velocities of the air vortex the intensity of the ascending fluid flow (axial reverse flow) is such that the annular partition floats up (because of the origin of pressure difference above and under the partition) to the surface of the cell suspension (the condition of optimum immersion of the annular partition $H \geq \geq 0.02(D_1-D_2)$ is disturbed, as a result of which the hydrodynamic mode of the flow (stirring) of the liquid (cell suspension) is disturbed, the conditions of aerating the cells being cultivated are worsened, this being followed by the precipitation of the biomass to the bottom of the reactor and death of the cells because of shortage in oxygen. On variations in the viscosity of the liquid phase in the process of cultivating biological objects, the annular partition, owing to its constant buoyancy, may uncontrollably change its position in relation to the surface of the liquid phase.

Besides, as the floating annular partition rotates in the cell suspension, stagnant shadow zones originate behind the floats, in which the cells being cultivated precipitate and accumulate. The lower layers of the cells perish in said zones because of shortage in oxygen, the quality of the finished product being thereby impaired and the technological characteristics of the apparatus lowered.

DISCLOSURE OF THE INVENTION

The present invention is directed to the provision of an apparatus for cultivating tissue cells or microorganisms in suspension which would ensure formation of an axial-symmetric vortex motion of liquid with axial reverse flow in the cell suspension without stagnant zones either at low velocities of gas movement (3–6 m/s) or at higher velocities thereof (7–10 m/s and more) above the surface of this liquid due to maintaining the annular partition at the optimal depth irrespective of changes in the intensity of the gas vortex above the surface of the cell suspension and changes in the viscosity of the liquid phase, which, in turn, will allow cultivating tissue cells or microorganisms having different oxygen requirements.

The set object is accomplished due to the fact that in an apparatus for cultivating tissue cells or microorganisms in suspension, which comprises a cylindrical reservoir with a cover and branch pipes, accordingly, for feeding an aerating gas and removing gaseous medium, and a device for aerating and stirring the suspension, comprising a horizontal blade wheel secured on a vertical hollow shaft and arranged in the top part of the reservoir directly under the cover, an annular partition installed in the cylindrical reservoir coaxially with the blade wheel with a clearance being formed between the cylindrical wall of the reservoir and the annular partition, and a mechanism for stabilizing the position of the annular partition with respect to the surface of the liquid phase (of the cell suspension), made in the form of guide elements and floats, according to the invention, the guide elements of the mechanism for stabilizing the position of the annular partition with respect to the surface of the liquid are made as detachable blades with a flat upper surface and a convex lower surface, said blades being oriented radially with respect to the annular partition and the surfaces of said blades defining an aerodynamic profile thereof of the "forward-sweep wing" type; the blades are attached with the help of struts to the upper surface of the annular partition or the blades are attached with the help of struts to the upper and lower surfaces of this partition, the blades being provided with units for varying the angle of attack with respect to the incoming flow of gas or liquid and for securing the blades to the struts on the annular partition and under it, respectively.

The aero- or hydrodynamic force originating as the blades of such design (with the profile of the "forward-sweep wing type) are streamlined by gas or liquid, is directed against the hydrodynamic force causing floating-up of the annular partition, and this allows said annular partition to be kept at an optimum depth when the velocity of the gas vortex above the surface of the liquid phase is greater than 6–7 m/s.

The units for varying the angle of attack with respect to the incoming flow of gas or liquid and for securing the blades to the struts on the annular partition and under it are made as clamping devices. Said units can be made as various plug-type connections, for instance, of the screw-nut or collet type.

When the blades on the annular partition are disposed above the surface of the cell suspension, the angle of attack of the blades with respect to the incoming flow of gas is from −15° to −90°, and when the blades are disposed in the liquid under the annular partition, the angle of attack of the blades with respect to the incoming flow of the liquid is from 0° to −35°.

In said angular ranges of inclination of the blades to the incoming flow of gas or liquid stable retention of the annular partition at an optimal depth with low power consumption is ensured.

The floats of the mechanism for stabilizing the position of the annular partition with respect to the surface of the liquid phase are made in the body of this partition. They are shaped as truncated unequal-sided pyramids oriented with the truncated vertexes toward the annular partition and fixed on the struts with a clearance in relation to the blades and the annular partition.

Such configuration of the floats ensures an increase in the reliability of maintaining the annular partition at an optimal depth irrespective of variations in the viscosity of the liquid phase, while the clearance between the floats and the annular partition eliminates stagnation shadow zones behind the floats, whereby settling, accumulation and death of the cultivated cells in these zones are prevented.

Arranging the floats in the body of the annular partition also eliminates stagnant shadow zones on this partition, whereby settling, accumulation and death of the cultivated cells in these zones are obviated.

The annular partition is immersed into the cell suspension to depth (H) equal to $H=0.02-0.09(D_1-D_2)$, where $D_1$ is the diameter of the annular partition;

$D_2$ is the diameter of the axial opening in the annular partition.

A decrease in the value $H<0.02(D_1-D_2)$ results in "locking" the drain of liquid through the axial opening in the annular partition, this leading to deterioration of the process of stirring and aerating the cultivated cells, with subsequent settling of the biomass to the bottom of the reactor and death of the cells because of shortage in oxygen. If the depth of immersion (H) of the annular partition is appreciably greater than $H=0.09(D_1-D_2)$, a travelling wave is formed above the surface of suspension, which gradually brings the whole mass or the cell suspension into rocking and then into the mode of unstable stirring with lowered mass-transfer parameters (auto-oscillation mode). This negatively influences the viability and productivity of the biomass.

BRIEF DESCRIPTION OF THE DRAWINGS

The invention will further be explained by the description of a particular embodiment thereof with the reference to the accompanying drawings, on which.

DESCRIPTION OF PREFERRED EMBODIMENT

Figure 1:
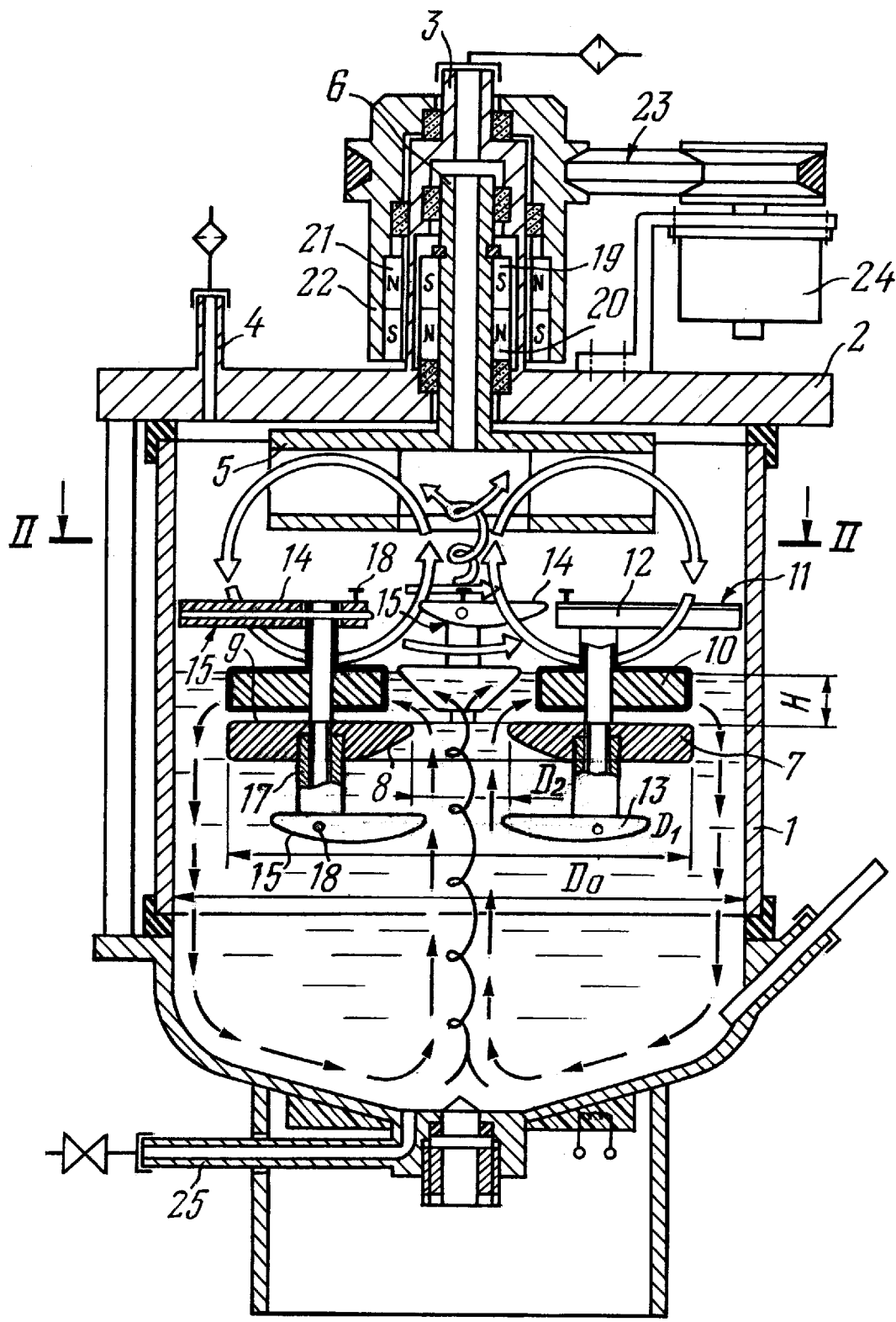
FIG. 1 is a diagrammatic view of an apparatus for cultivating tissue cells and microorganisms in suspension, with blades disposed above an annular partition, and floats disposed in the body of this partition.
Figure 2:
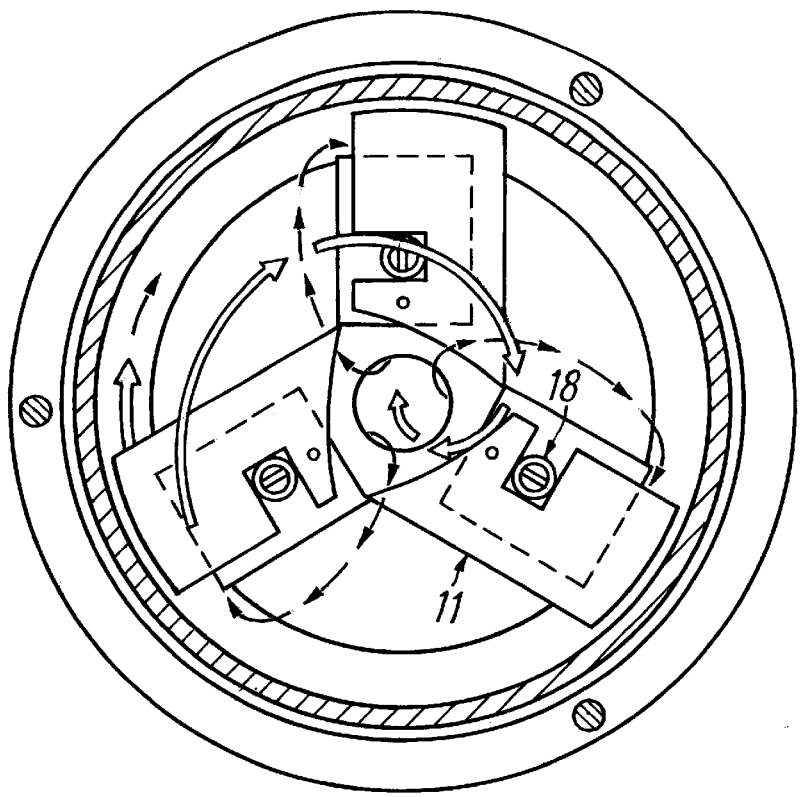
FIG. 2 is a sectional view of the apparatus, along A—A in FIG. 1.

The apparatus of the invention for cultivating tissue cells and microorganisms in suspension comprises a cylindrical reservoir 1 (FIG. 1) for a cell suspension, with a cover 2 and branch pipes 3 and 4 for supplying an aerating gas and removing gaseous medium, respectively, and a device for aerating and stirring the nutrient medium. The branch pipe 3 for supplying an aerating gas is installed above the cover 2 coaxially with the reservoir 1, and the branch pipe 4 for gas removal is installed on an edge of the cover 2. The device for aerating and stirring the cell suspension comprises a horizontal blade wheel 5 secured on a vertical hollow shaft 6 and arranged in the upper part of the reservoir 1 directly under the cover 2; an annular partition 7 installed in the reservoir 1 coaxially therewith and with the wheel 5, a clearance being provided between the cylindrical wall of the reservoir 1 and the annular partition 7; and a mechanism for stabilizing the position of the annular partition 7 with respect to the surface of the cell suspension.

Lower surface 8 of the annular partition 7 is convex, and upper surface thereof is flat. Furthermore, the annular partition 7 has a diameter ($D_1$) equal to $D_1=(0.7\div6.9)D_0$, the diameter ($D_2$) of the axial opening in the partition 7 is equal to $D_2=(0.1\div0.3)D_1$, where $D_0$ is the inner diameter of the cylindrical reservoir 1. The partition 7 should be immersed into the cell suspension to the depth (H) equal to $H==0.02-0.09(D_1-D_2)$ The mechanism for stabilizing the position of the annular partition 7 with respect to the surface of the cell suspension comprises floats 10 and guide elements 11. The guide elements 11 of the mechanisms for stabilizing the position of the annular partition 7 in relation to the surface of the cell suspension are made as detachable blades 12 and 13 with a flat upper surface 14 and a convex lower surface 15, said blades being oriented radially with respect to the annular partition and the surfaces of said blades defining an aerodynamic profile thereof of the "forward-sweep wing" type. Aerodynamic force $F_1$ originating as the blades 12 are streamlined by gas and hydrodynamic force $F_2$ originating as the blades 13 are streamlined by liquid, are directed against the hydrodynamic force $F_3$ which originates in the rotating stream of the liquid and causing floating-up of the annular partition 7 owing to the difference of pressures above and below this annular partition.

In one of the embodiments of the mechanism for stabilizing the position of the annular partition with respect to the surface of the liquid phase (FIG. 1) the blades 12 are installed with the help of struts 16 on the annular partition 7, and the floats 10 are made in the body of this annular partition 7.

In another embodiment of the mechanism for stabilizing the position of the annular partition with respect to the surface of the liquid phase (FIG. 3) the blades 12 are installed with the help of struts 16 on the annular partition 7, and the blades 13 are installed with the help of struts 17 above the annular partition 7. The floats 10 are attached to the struts 16 between the blades 10 and the annular partition 7 with the formation of clearances between the floats 10 and the partition 7, as well as between the floats 10 and the blades 12. The floats 10 are shaped as truncated unequal-sided pyramids oriented with the truncated vertexes toward the annular partition 7.

Figure 4:
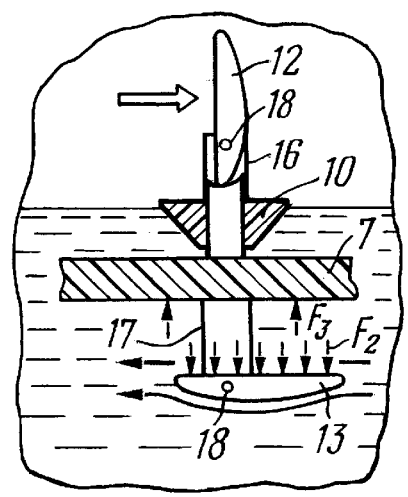
FIG. 4 shows a mechanism for stabilizing the position of the annular partition in relation to the surface of liquid, with floats disposed on struts, and blades disposed above the annular partition (with the angle of attack of the blades with respect to the gas flow of −90°) and under this partition (with a small angle of attack of the blades with respect to the flow of liquid).

In one of the modes of operation of the second embodiment of the mechanism for stabilizing the position of the annular partition with respect to the surface of the liquid phase (FIG. 4), the blades 12 are installed at the angle of −90° to the partition 7 and serve only for providing rotation of this partition in the liquid (in the cell suspension).

The blades 12 and 13 are provided with units for varying the angle of attack with respect to the incoming flow of gas or liquid and for securing the blades to the struts 16 on the annular partition 7 and to the struts 17 under the annular partition 7, respectively. The units for varying the angle of attack of the blades 12 and 13 with respect to the incoming flow of gas or liquid and for securing them, respectively, to the struts 16 and 17 are made as clamping devices 18 of the screw-nut or collet type.

The angle of attack of the blades of 12 with respect to the incoming flow of the gas is from −15° to −90°, and the angle of attack of blades of the blades 13 with respect to the incoming flow of the liquid is from 0° to −35°.

The annular partition 7 is immersed into the cell suspension to the depth (H) equal to $H=0.02-0.09(D_1-D_2)$ where:

$D_1$ is the diameter of the annular partition;

$D_2$ is the diameter of the axial opening in the annular partition.

For rotation of the blade wheel 5 a magnetic coupling 19 is used, one of the moving parts 20 of which is mounted on the hollow shaft 6 above the cover 2, and the other part 21 is disposed on a hollow axle 22. The hollow axle 22 is disposed coaxially with the shaft 6 around the moving part 20 of the coupling 19. The part 20 of the coupling 19 is brought in rotation, for example, through a belt transmission 23 by the electric motor 24. In the bottom part of the reservoir 1 (in FIG. 1) a branch pipe 25 is disposed for the admission of the cultural medium and the inoculum. The same branch pipe 25 serves for draining the cell suspension on completion of the cultivation process.

Figure 3:
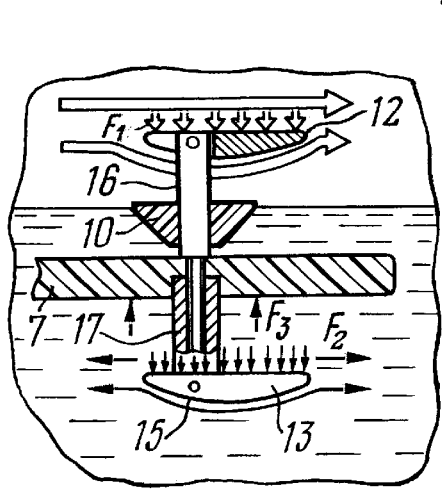
FIG. 3 shows a mechanism for stabilizing the position of the annular partition in relation to the surface of liquid, with floats disposed on struts, and blades disposed above the annular partition and under it (the blades have small angles of attack with respect to the flow of gas and liquid)

The proposed apparatus operates as follows:

For cultivating highly aerobic biological objects (cells of animals or insects), the blades 12 are installed with the help of the clamping devices 18 on the struts 16 of the annular partition 7 with the angle of attack, for instance, of −35° (FIG. 1), or the blades 12 are installed on struts 16 with the angle of attack of the blades 12, for instance, of −25°, and the blades 13 on the struts 17 of the annular partition 7 with the angle of attack of the blades 13, for instance, of −15° (FIG. 3).

For cultivating low-aerobic biological objects (some types of bacteria), the blades 12 are installed with the help of the clamping devices 18 on the struts 16 of the annular partition 7 with the angle of attack, for example, of −16° (FIG. 1), or the blades 12 are installed on the struts 16 of the annular partition 7 with the angle of attack, for example, of −16° and the blades 13 are installed on the struts 17 of the annular partition 7 with the angle of attack of the blades 13, for instance, of 0° (FIG. 3).

After that the cylindrical reservoir 1 with the installed annular partition 7 and the mechanism for stabilizing its position with respect to the surface of the liquid is filled with the nutrient medium under sterile conditions so that a space should be left above the surface of the medium in the upper part of the reservoir 1 for movement of the aerating gas, and the annular partition 7 be disposed on the surface of or at a certain depth in the nutrient medium (by selecting the buoyancy of the floats 10), which is less than the optimum depth $H=0.02-0.09(D_1-D_2)$. The blades 12 in this case are disposed above the surface of the liquid. For example, for the reservoir with the diameter $D_0=200$ mm the optimum parameters of the apparatus are as follows: $D_1=160$ mm; $D_2=32$ mm; $H=8$ mm. Further, the temperature regime required for cultivating cells or microorganisms is set up, the necessary dose of inoculum is introduced, and the electric motor 24 is switched on. The necessary number of revolutions of the blade wheel 5 is set, depending on the requirements of the cultivation technology requirements. When the blade wheel 5 rotates above the surface of the nutrient medium with the inoculum, a rarefaction is created in the zone close to the axis of the reservoir 1 and an elevated pressure is created on the periphery of this reservoir. Under the effect of the pressure difference between the periphery and the zone close to the axis of the gas space, a swirling flow of the aerating gas is formed above the surface of the liquid, with the field of potential vortex velocity on the periphery of the reservoir 1 and an axial reverse flow in the zone near the axis thereof, which generates in the liquid a similar turbulent rotary motion with intensive stirring along the axis of the reservoir.

When cultivating low-aerobic biological objects, for instance, some types of bacterial cells, the rotation velocity of the gas vortex is set to be 3–6 m/s. In this case there is generated aerodynamic force $F_1$ (it originates as the blades 12 are streamlined by the gas flow) or aerodynamic force $F_1$ and hydrodynamic force $F_2$ are generated (the latter force originates as the blades 13 are streamlined by the liquid flow), or hydrodynamic force $F_2$ alone is generated. Said forces $F_1$ (FIG. 1) or $F_1$ and $F_2$ (FIG. 3), or $F_2$ (FIG. 4) additionally immerse the annular partition 7, setting it at the optimal depth (H), which is in the range of depths $H=0.02-0.09(D_1-D_2)$.

When cultivating highly aerobic biological objects, for instance, plant or animal cells, the rotation velocity of the gas vortex is set to be higher than 7–10 m/s. With such velocities of the gas vortex, the annular partition 7 which is in the rotating stream of liquid, is acted upon not only by the forces $F_1$ (FIG. 1), or $F_1$ and $F_2$ (FIG. 3), or F (FIG. 4) directed vertically downwards, but also by additional hydrodynamic force $F_3$ (owing to the origination at such velocities of a flow of liquid stemming from the difference in pressures above the partition 7 and below it), said force $F_3$ being directed vertically upwards and causing the partition 7 to float up. The force $F_3$ compensates partly for the action of the forces $F_1$ and $F_2$, and the annular partition 7 retains reliably its position in the range of depths $H=0.02-0.09(D_1-D_2)$.

Thus, the mechanism for stabilizing the position of the annular partition 7 allows to maintain it at the optimal depth (H) irrespective of the mode of cultivating or the volume of suspension in the apparatus. Owing to the installation of the annular partition 7 in the suspension, the intensity and directivity of its ascending and descending streams is increased (i.e., the efficiency of the gas vortex is increased).

According to calculations, at the average gas flow velocity above the surface of suspension $V_{gas}=10$ m/s, the average rotation rate of the blades 12 together with the annular partition 7 ($D_1=160$ mm) with respect to the liquid will be $V_{part.}=2.446$ m/s, and force $F_3=0.393$ N.

With the length of the blades 12 $l_1=7.5$ cm and the chord $h_1=2$ cm; with their number $n_1=3$; with the angle of attack of the blades 12 with respect to the gas flow $\alpha_1=-35°$, force $F_1==0.4873$ N. Thus, in the embodiment of the mechanism for stabilizing the position of the annular partition 7 with respect to the surface of the liquid, shown in FIG. 1, the force $F_1$ is partially compensated for by the action of the force $F_3$ and said partition will reliably retain its position at the depth H.

With the length of the blades 13 $l_2=3.0$ cm and the chord $h_2=1.5$ cm; the number of the blades $n_2=6$; the angle of attack of the blades 13 with respect to the liquid flow $\alpha_2=0°$ the force $F_2=0.4845$ N. Therefore, in the embodiment of the mechanism for stabilizing the position of the annular partition 7 with respect to the surface of the liquid, shown in FIG. 4, the force $F_2$ will be partially compensated for by the action of the force $F_3$, and said partition will reliably retain its position at the depth H. Besides, stability of the position of the annular partition 7 in the given embodiment of the mechanism is supported by varying the buoyancy of the floats 10.

The floats 10 configured as unequal-sided truncated pyramids also allow to maintain the annular partition 7 at the optimal depth irrespective of the mode of cultivating or the volume of the cell suspension in the apparatus, since in case the partition 7 happens to float up to some extent, say, because of an increase in the velocity of the gas vortex or in the density of the cell suspension in the course of cultivation, the buoyancy of the floats 10 decreases (owing to their specific shape), and the partition 7 again returns to the depth (H).

Arranging the floats 10 in the body of the partition 7 (FIG. 1) or setting a clearance between the floats 10 and the annular partition 7 (FIGS. 3, 4) provides elimination of stagnant (shadow) zones on the surface 9 of the partition 7, and also prevents settling, accumulation and death of cultivated cells in said zones.

In the process of cultivating cells or microorganisms the aerating gas interacts with the liquid phase through its free surface above the annular partition 7 without mixing with the liquid. Therefore, no gas bubbles are present in the cell suspension, so that traumatizing of the cells and formation of foam are ruled out. At any velocity of the gas vortex, at least in the range of 3–20 m/s, detachment of suspension drops from the suspension surface does not occur, and traumatizing of cells is additionally reduced.

Due to rarefaction in the zone close to the axis of the blade wheel 5, additional inflow of the aerating gas to the reservoir 1 is effected through the branch pipe 3, and owing to an increased pressure on the periphery of the gas space above the surface of the suspension, the outflow of the gaseous medium from the reservoir 1 is effected through the branch pipe 4. An optimal ratio of the aerating gas components for the provision of normal conditions of cultivating cells or microorganisms is achieved.

Thus, the proposed design features of the apparatus of the present inventions with different embodiments of the mechanism for stabilizing the position of the partition 7 with respect to the liquid medium makes it possible to ensure formation of an axial-symmetric rotary motion of liquid with axial reverse flow in the cell suspension without stagnant zones either at low velocities of gas movement (3–6 m/s) or at higher velocities thereof (7–10 m/s and more) above the surface of this liquid due to maintaining the annular partition at the optimal depth irrespective of changes in the intensity of the gas vortex above the surface of the cell suspension. This, in turn, allows cultivating tissue cells or microorganisms sensitive to mechanical traumatizing and having different oxygen requirements, as well as attaining a higher concentration of any types of cells in suspension.

Industrial Applicability

The proposed apparatus for cultivating tissue cells and microorganisms in suspension can be widely used in microbiological, medical and foodstuffs industry.

What is claimed is:

1. An apparatus for cultivating tissue cells or microorganisms in suspension, comprising a cylindrical reservoir, a cover for the cylindrical reservoir, branch pipes for supplying an aerating gas and removing gaseous medium and a device for aerating and stirring the gaseous medium, the device comprising a horizontal blade wheel secured on a vertical hollow shaft and arranged in an upper part of the reservoir directly under the cover, an annular partition installed in the cylindrical reservoir coaxially with the blade wheel with a clearance between the cylindrical wall of the reservoir and the annular partition, and a mechanism for stabilizing the position of the annular partition with respect to the surface of the cell suspension, said mechanism comprising guide elements and floats, the guide elements being formed as detachable blades including an upper blade and a lower blade having air foil shapes with a flat upper surface and a convex lower surface, the upper blade being attached by first struts to the annular partition and the lower blade being attached to the partition by second struts, the blades being provided with units for varying an angle of inclination of the blades with respect to an incoming flow of gas or liquid.

2. An apparatus for cultivating tissue cells or microorganisms in suspension, comprising a cylindrical reservoir for containing a cell suspension;

a cylindrical wall of said cylindrical reservoir;

an upper part of said reservoir;

a cover for said cylindrical reservoir;

a branch pipe arranged on said cover for supplying an aerating gas to said cylindrical reservoir;

a device for stirring cell suspension and aerating gas;

a vertical hollow shaft of said device fixed in the cover of said cylindrical reservoir;

a horizontal blade wheel of said device secured on said vertical hollow shaft and arranged in said upper part of said cylindrical reservoir directly under the cover;

an annular partition of said device fixed in said cylindrical reservoir coaxially with the blade wheel;

an upper surface of said annular partition;

a lower surface of said annular partition;

a mechanism for stabilizing the position of the annular partition with respect to the surface of the cell suspension;

guide elements of said mechanism for stabilization;

floats of said mechanism for stabilization;

first blades comprised in said guide elements, and being detachable, oriented radially with respect to the annular partition and positioned above said floats with respect to the cell suspension surface, each of said blades having a flat upper surface facing said blade wheel and a convex lower surface facing said floats, wherein the flat upper surface and the convex lower surface of each blade form an aerodynamic profile of “forward-sweep wing” type;

second blades being detachable and oriented radially with respect to the annular partition and positioned under said floats with respect to the cell suspension surface; each of said blades having a flat upper surface facing said annular partition and a convex lower surface facing in the direction from the annular partition, wherein the flat upper surface and the convex lower surface of each said blade form an aerodynamic profile of a "forward-sweep wing" type;

first struts for attaching said first blades to said upper surface of said annular partition;

second struts for attaching said second blades to said lower surface of said annular partition; and a unit for varying an angle of inclination with respect to the incoming flow of gas or liquid and for securing each of said first blades and said second blades to the struts.

3. An apparatus according to claim 2, wherein said unit for varying the orientation of the blades with respect to the incoming flow of gas or liquid comprises clamping devices.

4. An apparatus according to claim 2, wherein the orientation angle of the first blades is from about −15° to about −90° and the orientation angle of said second blade is from about 0° to about −35°.

5. An apparatus according to claim 2, wherein said annular partition comprises a body containing said floats of said mechanism for stabilizing.

6. An apparatus according to claim 2, wherein said annular partition is immersed into cell suspension to the depth equal to $0.02D_1$–$0.09D_2$ where $D_1$ is the diameter of said annular partition;

$D_2$ is the diameter of the axial opening of said annular partition.

* * * * *